United States Patent [19]

Whitman, III

[11] 4,218,606

[45] Aug. 19, 1980

[54] APPARATUS FOR PERFORATING WEBS WITH HIGH INTENSITY, COHERENT RADIATION

[75] Inventor: Hobart A. Whitman, III, Asheville, N.C.

[73] Assignee: Olin Corporation, Pisgah Forest, N.C.

[21] Appl. No.: 948,108

[22] Filed: Oct. 3, 1978

[51] Int. Cl.² .............................................. H05B 9/00
[52] U.S. Cl. ................................................ 219/121 L
[58] Field of Search ............. 219/121 L, 121 LM, 384

[56] References Cited

U.S. PATENT DOCUMENTS

| | | | |
|---|---|---|---|
| 2,528,157 | 10/1950 | Menke | 219/384 |
| 3,226,527 | 12/1965 | Harding | 219/121 L |
| 4,025,752 | 5/1977 | Whitman | 219/384 |
| 4,032,743 | 6/1977 | Erbach et al. | 219/121 LM |
| 4,063,064 | 12/1977 | Saunders et al. | 219/121 LM |
| 4,118,619 | 10/1978 | McArthur et al. | 219/121 L |
| 4,121,595 | 10/1978 | Heitmann et al. | 219/121 L |

Primary Examiner—B. A. Reynolds
Assistant Examiner—Clifford C. Shaw
Attorney, Agent, or Firm—Harold L. Stowell

[57] ABSTRACT

A system is provided for controlling the porosity of a web or film as perforated by high intensity, coherent radiation. In particular, there is included a laser for providing at least one beam of high intensity, coherent radiation that is directed onto a web that is moved past the beam. The porosity of the web is measured and compared with an operator-set reference of porosity to control the focus of the coherent radiation, whereby the size of the resultant perforation and therefore the porosity of the web is controlled. In one embodiment of this invention, the position of a lens to focus the coherent radiation is adjusted. In a further embodiment, a support surface for receiving the web is adjusted with respect to the fixed focus laser beam to control the size of the perforation or opening created by the beam of coherent radiation.

13 Claims, 8 Drawing Figures

VARYING PARAMETER

FIG. 5A.

MOVING WEB

APPARATUS FOR PERFORATING WEBS WITH HIGH INTENSITY, COHERENT RADIATION

BACKGROUND OF THE INVENTION

1. Field of the Invention

This invention relates generally to a system and method for perforating a web or film with a beam of high intensity, coherent radiation and for controlling the resultant porosity of the web to provide a precisely-controlled, uniform porosity of the finished product.

2. Description of the Prior Art

The prior art has described as in U.S. Pat. No. 4,025,752 by the inventor of this invention and assigned to the assignee of this invention, a system for controlling the porosity of a web or film by controlling the frequency or pulse width of an electric spark passing between electrodes and through the web. The web is driven past the pair of electrodes and the resultant porosity is measured to be compared with a reference set point to develop an error signal. The resultant error signal is multiplied with a signal indicative of web speed to control the frequency or pulse width of a pulse generator, which is connected to cause arcing between the aforementioned electrodes.

Further, the prior art discloses the use of a high intensity, coherent beam of radiation such as produced by a laser to perform various machining functions including cutting or placing holes in materials including webs of materials directed therepast. For example, U.S. Pat. No. 4,063,064 of Saunders et al. discloses apparatus for precisely forming holes by laser beams within work pieces such as pills. The work piece is moved past the laser beam directed onto the work piece, and the size of the hole is controlled by controlling the focus of the laser beam, and in particular by controlling the distance between a focusing lens and the work piece, whereby the diameter of the beam and therefore the resultant hole may be controlled.

In U.S. Pat. No. 4,032,743 of Erbach et al., there is disclosed a method and apparatus for forming rows and columns of closely spaced holes within a thin foil, whereby the resultant porosity in terms of percentage of openness may be controlled. In particular, the thin film is rotated by a drum past a series of lasers whose focal distance from the foil is controlled by means of micrometer threads to thereby control the size of the openings within the foil. The frequency of the laser firing is controlled by applying a track of magnetic data upon an end portion of the drum that is sensed magnetically to provide control signals to turn on and off the lasers, whereby the center-to-center spacing and the row spacing of the resultant holes is controlled. In a further embodiment, a rotating disk is used to interrupt a light source whereby control signals are developed to control the laser firing and therefore the center-to-center and row spacing. However, there is no means for directly sensing or measuring the porosity, and the percentage of openness of the film is controlled by determining the size of the opening, as well as the center-to-center spacing of the openings and the spacing between rows. Once the focus and therefore the size of the opening formed by the laser beam is set, it is no longer adjusted.

Further, in U.S. Pat. No. 3,226,527 of Harding, there is disclosed apparatus for perforating a sheet material that is directed past an array of lasers. In a further embodiment, there is suggested that a single laser be scanned across the lateral dimension of the web as it is directed past the scanning laser. The spacing between the perforations is controlled by a rotating mechanical shutter that is rotated in synchronism with the speed at which the web is directed past the laser beam. The mechanical shutter is rotated by a motor and has openings to permit the passage of the laser beam onto the web to be perforated. By controlling the relative rates of interruption of the laser beam and the speed at which it is directed therepast, the spacing between perforations is controlled.

It is noted that the above-described apparatus and methods of the prior art does not directly measure porosity but rather controls porosity by controlling the size of the perforations as well as the spacing therebetween. Thus, the prior art assumed that hole density and thus porosity could be controlled by varying the laser pulse frequency relative to web speed. However, since the continuous laser beam is multiplexed, i.e, is shuttered on and off as suggested by U.S. Pat. No. 3,226,527, it has been discovered by this invention that the ratio of perforated area to unperforated area remains unchanged regardless of the pulse rate and/or web speed. This is may be understood from the following observations. If for example, the rate of perforation is increased by increasing the speed of the mechanical shutter, there will be no substantial change in the resultant web porosity. First consider if the frequency is increased, the length of time that a portion of the web is exposed to the laser beam is decreased and therefore the resultant size of the hole is decreased. Thus, though the frequency or number of holes increases, the resultant size decreases thereby tending to maintain the resultant porosity of the web constant. Conversely, if the speed of rotation of the mechanical shutter is decreased, the length of exposure to the beam of radiation and thus the resultant size of the perforation is increased. Though the size of the opening is increased, the number of such openings or perforations is decreased thus tending to maintain the resultant porosity constant. However, there will be a slight change in web porosity at moderately high and low web speeds and pulse rates. This is due to the limited burn duration of each pulse applied to the moving web which, itself, exhibits varying degrees of thermal inertia.

SUMMARY OF THE INVENTION

Thus, it is an object of this invention to control the percentage of hole area or porosity, independently of work piece speed and/or frequency of coherent radiation pulsing.

It is a further object of this invention to control precisely the porosity of a work piece, e.g., a web as it is directed past an intermittent beam of coherent radiation in a manner to compensate for variations in work piece speed, frequency of the pulse coherent radiation, power of the radiation and thickness or density of the work piece.

In accordance with these and other objects of the invention, there is provided a method and apparatus for accurately controlling the porosity of a work piece and in particular, a web as it is directed past a source of a focused beam of coherent radiation. A measure of the resultant work piece porosity is made and is compared against a reference set point to provide an error signal. A mechanism is responsive to the error signal to adjust the relative spacing between the focus point of the coherent radiation and the web, whereby the cross sectional area of the diverging beam of coherent radiation with respect to the work piece and thus the area of the perforation within the work piece is adjusted.

In one illustrative embodiment of this invention, the mechanism is coupled to move a platform carrying the work piece past a fixed focused beam of coherent radiation to adjust the relative position with respect to the fixed focused beam or source of coherent radiation.

In a further embodiment of this invention, the mechanism is coupled to a focusing means and in particular a lens for varying the position of the lens and thus the cross sectional area of the beam with respect to the work piece.

BRIEF DESCRIPTION OF THE DRAWINGS

Further advantages and uses of this invention will become more apparent when considered in view of the following detailed description and drawings, in which.

DETAILED DESCRIPTION OF THE PREFERRED EMBODIMENT

Figure 1:
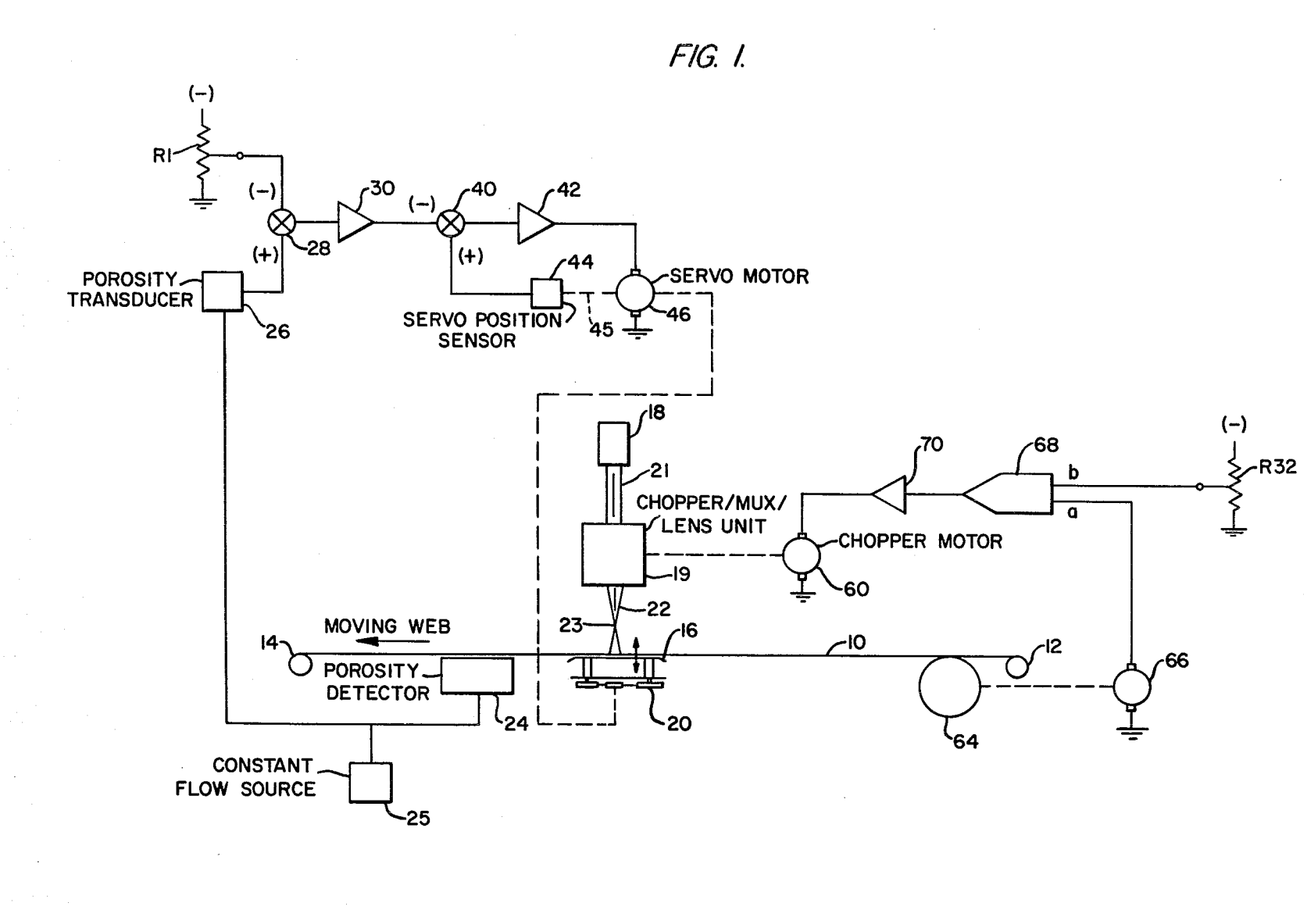
FIG. 1 is a general, functional block diagram of a system incorporating the teachings of this invention.

With regard to the drawings and in particular to FIG. 1, there is shown a system for controlling the porosity of a web 10 as it is directed past a plurality of beams 22 of focused coherent radiation as generated by a laser source 18. The work piece to be perforated, illustratively in the form of a web 10 is driven from a supply roll 12 to a take-up roll 14. A shutter mechanism 19, to be explained in detail later, chops, multiplexes and focuses a single, continuous beam 21 of coherent radiation derived from the source 18 into a plurality, e.g., 4, of beams 22 to be directed upon the web 10. The web 10 is directed over a platform 16 that is movable in a vertical direction as shown in FIG. 1 by a mechanical translator 20 that is coupled to the platform 16. As a part of the mechanical shutter 19, there is included an optical multiplexer to split the beam 21 into a plurality of beams 22. Further, the mechanical shutter 19 also includes lenses for focusing the plurality of beams 22 of radiation to focus points 23 from which they diverge onto the web 10. It is understood that the web 10 may be of any material including thin plastic films, paper, or any like material that is capable of being "drilled" by the beams 22 of focused coherent radiation.

The shutter mechanism 19 interrupts the continuous output of the source 18 of coherent radiation, whereby the resultant beams 22 of focused coherent radiation are pulsed at a predetermined frequency that is adjusted with respect to the velocity of the web 10 as driven by a motor 60, as shown in FIG. 1. By so synchronizing the pulse rate of the beams 22 with respect to the web velocity, the number of perforated holes for a unit length of the web is set. In an illustrative embodiment of this invention, the mechanical shutter and multiplexer 19 produces four beams 22 of radiation that are disposed laterally across the width of the web 10.

As shown in FIG. 1, a porosity detector 24 is disposed downstream of the beams 22 of radiation to measure the resultant porosity of the web 10. A transducer 26 is associated with the porosity detector 24 to provide an output electrical signal indicative of the resultant porosity to be compared to a reference set point established by the potentiometer R1 and adjusted by the setting of its movable contact. The outputs of the transducer 26 and the reference set point are compared by a summing circuit 28 to produce an error signal that is amplified by a suitable amplifier 30 to be applied to a second summing circuit 40 to be compared with an output of a servo-position sensor 44. The output of the second summing circuit 40 is further amplified by a servo-amplifier 42 before being applied to a servo-motor 46 that is mechanically coupled to drive the mechanical translator 20, whereby the position of the platform 16 is raised or lowered dependent upon the error signal derived from the servo-amplifier 42. The position of the servo-motor 46 and the platform 16 is provided by the servo-position sensor 44 that is connected by a coupling 45 to the servo-motor 46, to provide an output signal applied to an input of the second summing circuit 40, whose output signal is indicative in amplitude of the desired adjustment in the position of the platform 16 and whose polarity is indicative of the direction in which the platform 16 is to be moved by the servo-motor 46.

Further with respect to FIG. 1, the web 10 is driven over a web drive roll 64 rotating it at an angular velocity dependent upon the linear velocity of the web 10. The roll 64 is coupled to a web speed tachometer 66, which provides an output signal indicative of the linear web velocity to be applied to a first input of a multiplier 68. A potentiometer R32 is provided and its contact is set dependent upon the desired ratio of chopper rotational speed and pulse frequency to web speed; the potentiometer R32 applies a corresponding voltage to a second input b of the multiplier 68. The output of the multiplier 68, which multiplies the web speed by the ratio of desired chopper speed to web speed, is an indication of chopper speed and is applied to a chopper motor power amplifier 70 which applies an amplified signal to a chopper motor 60. The motor 60 rotates the blades of a chopper to thereby split and pulse the beam 21 of coherent radiation emanating from its source 18, into a plurality of beams 22 to be directed unto the web 10.

Figure 3:
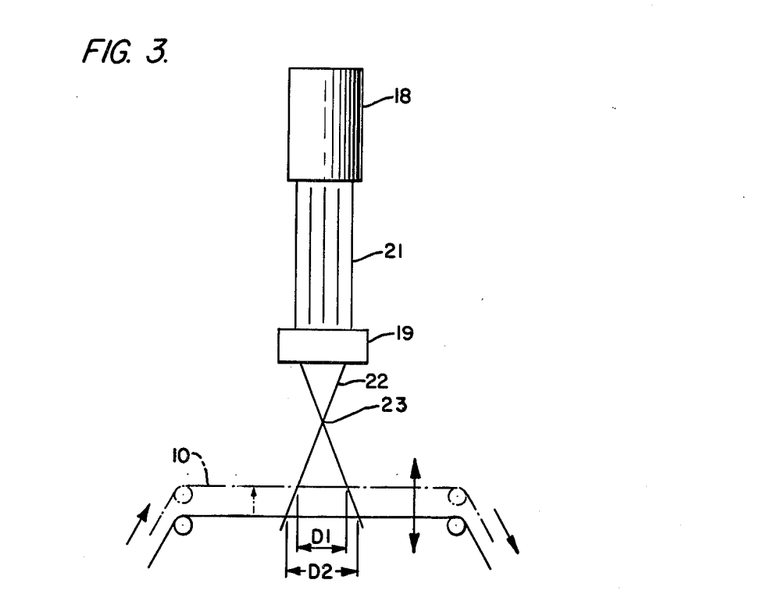
FIG. 3 is a side view of one illustrative embodiment of this invention wherein the position of a platform carrying the work piece to be perforated is varied with respect to a beam of coherent radiation.
Figure 4:
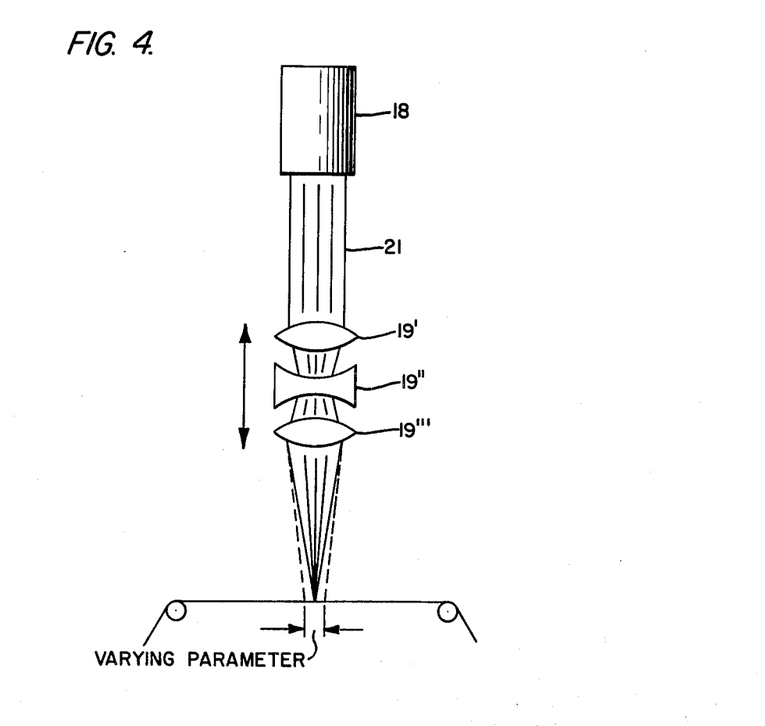
FIG. 4 illustrates a second illustrative embodiment of this invention, wherein the position of a lens with respect to the beam of coherent radiation is varied with respect to the position of the work piece to be perforated.

The basis of the operation of the system as shown in FIG. 1 is that of controlling the perforated hole area of the web 10 independently of web velocity or the pulse rate (or frequency) of the beams 22 of coherent radiation. As shown in FIG. 1, a feedback is used to compensate for the variations in web speed as well as other variables to change the cross sectional area of the beams 22 of focused coherent radiation and the resultant hole area. The described feedback loop is used to control the position of the platform 16 in a direction parallel to that of the focused beams 22 of coherent radiation. As indicated in FIGS. 1 and 3, the platform 16 positions the web 10 in the converging portion of beams 22 past the focus point 23. Since the platform 16 positions the moving web 10 in the convergent portion of the beams 22 each having a fixed focal point 23, the resulting cross sectional area of the opening or hole within the web 10 corresponds to the cross sectional area of the beam or cone of coherent or laser radiation at the point the beam 22 intersects the web 10. The ratio of the perforated to the unperforated area and thus web porosity is therefore dependent upon the platform position.

The first summing circuit 28 compares a signal indicative of the measured porosity with a set point indicative of the desired perforated web porosity. Any difference between the desired and measured signal provides an error signal which is amplified by the amplifier 30 to energize a servo-motor 46, whereby the platform is lowered or raised by a mechanical translator 20 and the web is repositioned with respect to the converging beam of coherent radiation. As the platform 16 is raised as shown by the arrow in FIG. 3, the cross section of the converging beams 22 decreases and as the platform 16 is lowered, the cross sectional area of the converging beams 22 of radiation increases. In this regard, note that the web 10 is disposed on the diverging side of the focus points 23, as shown in FIG. 3. Since the feedback signal responds to web porosity, compensation for the aforementioned variables is achieved through the use of the resultant error signal and the subsequent positioning of the web with respect to the beams 22 of coherent radiation.

As will be explained in greater detail with respect to FIGS. 6A and 6B, the beam 22 of coherent radiation is split into a plurality of beams 22 by a series of mechanical choppers each taking the form of a plurality of blades radiating from a center point and rotating past the beam 22 whereby it is alternately reflected onto the web 10 and permitted to pass through the space between the blades. The rate of interruption or pulse rate of the laser beam 22 is determined by the angular velocity of the chopper motor 60. It is desired to control the pattern of perforated holes or the number of perforated holes per linear dimension of web travel. To this end, the ratio of perforated holes to linear dimension of the web is controlled by the setting of the potentiometer R32. A signal indicative of web velocity is derived from the transducer 66 and is multiplied with the signal indicative of the desired ratio to obtain an output signal that is amplified by amplifier 70 to control the speed of the chopper motor 60. The result is synchronous tracking between the laser pulse rate and the web speed. The synchronized ratio or pattern and perforated holes per linear web travel is determined and adjusted by the ratio of chopper speed to web speed as set by the potentiometer R32.

Figure 2:
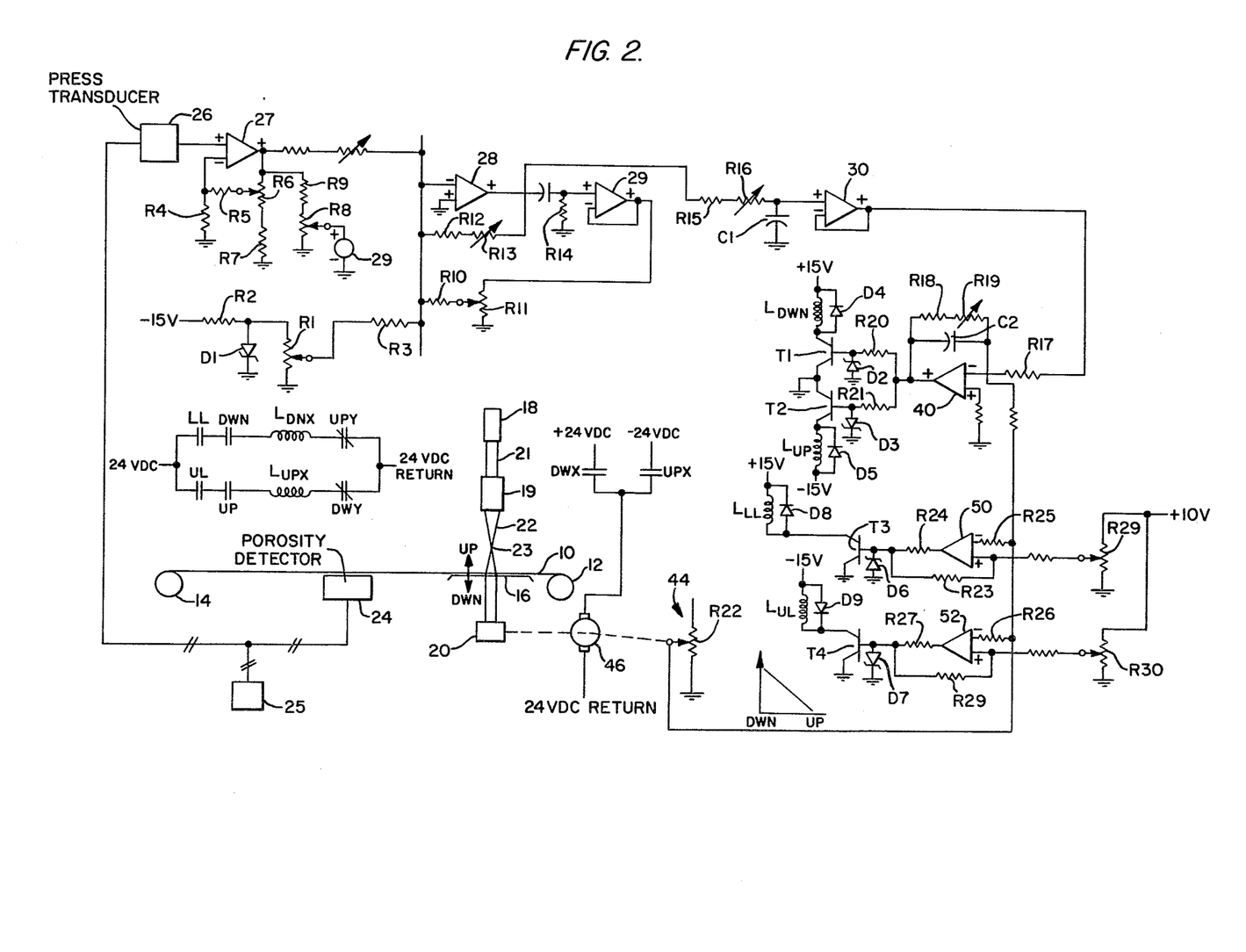
FIG. 2 is a detailed schematic drawing of the beam focusing control system of this invention as generally shown in FIG. 1.

Referring now to FIG. 2, there is shown a detailed circuit schematic of the system as generally shown in FIG. 1, wherein similar elements are identified with like numerals. The porosity detector 24 takes the form of a vacuum chamber disposed closely adjacent the web 10 and is coupled to a constant flow of vacuum source 25 by a conduit to establish a vacuum within the detector or chamber 24. Further, this conduit is coupled to the pressure transducer 26 which senses the variation in pressure within the chamber 24 and therefore the porosity of the web 10 to provide an output signal indicative thereof, to a first input of an operational amplifier 27. The gain of the operational amplifier 27 is controlled by a resistive network comprised of resistors, R4, R5, R6 and R7 and in particular by setting the contact of the potentiometer R6, whereby the output of the transducer may be standardized. Further, an indication of porosity is provided by a porosity meter 29 coupled via a potentiometer R8 and resistor R9 to the output of the operational amplifier 27. The output of the operational amplifier 27 is applied to an input of the operational amplifier 28 to be compared with a reference or set point as provided from the contact of potentiometer R1. As shown in FIG. 2, a potential is applied via resistor R2 across a reference voltage means in the form of a Zenor diode D1 to establish a relatively fixed voltage across the variable resistor R1. The operational amplifier 28 provides an error signal indicative of the difference between the reference set point and a measured value of web porosity. The stability of the operational amplifier 28 is enhanced by a feedback loop including operational amplifier 29 that is fed back through a potentiometer R11 and fixed resistor R10 to an input of the operational amplifier 28, whereby the stability of the feedback loop is set by varying the contact of the potentiometer R11. Further, a gain feedback loop comprised of potentiometer R13 and resistor R12 is formed between the output and an input of the operational amplifier 28; the gain thereof is set by varying the resistance of the potentiometer R13.

The output of the operational amplifier 28 is applied to the error signal gain amplifier 30 via a transportation lag network comprised of resistors R15, R16 and capacitor C1 to a first input of the amplifier 30. The potentiometer R16 is adjusted to provide a varying degree of lag so that an instantaneous change of the output signal derived from the pressure transducer 26, indicating a rapid change of porosity would not unduly effect the action of the servo-motor 40.

The output of the error signal gain amplifier is applied to a first input of a difference circuit or operational amplifier 40, whose gain is set by a network connected between the first input and an output and comprised of series connected resistors R18 and R19 coupled in parallel with a capacitor C2. As explained previously with respect to FIG. 1, an input indicative of the position of the motor 46 is provided from the servo-position sensor 44 taking the form of a potentiometer R22 mechanically coupled to the output drive shaft of the servomotor 46. As the motor 46 rotates in either direction, the position of the contact of the potentiometer R22 varies whereby a voltage is applied to the input of the operational amplifier 40 indicative of the position of the servo-motor 46 and thus of the platform 16.

The output of the operational amplifier 40 is coupled to a first transistor T1 which upon being rendered conductive energizes an actuating coil LDWN, which in turn closes the normally opened contact DWX. Further, the output of the amplifier 40 is also coupled to a second transistor T2 for energizing a coil $L_{UP}$ for closing the normally opened contact UPX. To protect the transistor bases from reverse voltages, a diode D2 is connected between the base of transistor T1 and ground, whereas a diode D3 is coupled between the base of transistor T2 and ground to protect the transistor bases from reverse voltages. Protective diodes D4 and D5 are respectively coupled in parallel with coils $L_{DWN}$ and $L_{UP}$. As will be explained in detail later, upon the closing of one of contacts UPX and DWX, its corresponding coil DWX and UPX is energized by the potential coupled thereacross to close the contact DWX or UPX, whereby the motor 46 is respectively driven to lower or to raise the platform 16.

As shown in FIG. 2, there is provided circuits for setting limits past which the platform 16 may not be driven. To this end, the output of the potentiometer R22 is coupled via an operational amplifier 50, resistor R24 to a third transistor T3, whose collector is coupled to a coil $L_{LL}$ protected by a diode D8. A second input to the amplifier 50 is coupled to a resistor R29 across which is disposed a potential and whose variable contact is set dependent upon the desired lower limit for the platform 16. As will be explained in detail, when the lower limit is reached by the platform 16, the transistor T3 ordinarily conducting is rendered non-conductive, whereby the coil $L_{LL}$ is deenergized to open the contact LL whereby the servo-motor 46 is de-energized.

Similarly, the output of the potentiometer R22 is coupled to a further operational amplifier 52 whose output is coupled via resistor R27 to the base of transistor T4, whose collector serves upon being rendered conductive to energize a coil $L_{UL}$ as protected by diode D9. A second input to the operational amplifier 52 is coupled to the contact of a potentiometer R30, which is varied to set the high limit of the platform 16. Similarly, when the high limit is exceeded, an output is developed from the amplifier 52 rendering non-conductive the transistor T4, thus deenergizing the coil $L_{UL}$ to open contact UL whereby the servo-motor 46 is de-energized.

The operation of FIG. 2 will now be described in detail. A set point representative of a desired porosity is derived from resistor R1 and is compared at the input of amplifier 28 with a signal inversely proportional to detected porosity from amplifier 27. As web porosity increases, the constant flowing vacuum pressure decreases at the detector 24 and the pressure transducer 26. The opposite holds true for porosity decrease. The result is a low positive signal from amplifier 27 for high detected porosities and a high positive signal for low detected porosities. This circuit is designed so that a slightly positive error will always exists between the negative signal from the resistor R1 and the positive signal from amplifier 27. Should a negative error momentarily appear, servo action and adjustment will be initiated until a positive error is re-established and balance is resumed. Detected porosity will ultimately and always follow set point changes and hold to its fixed reference through the action of the system of FIGS. 1 and 2.

Amplifier 28 acts as an inverting amplifier which provides a negative output for system operation and balance. This output varies illustratively from zero to minus ten volts and is conditioned for stability and transportation lag via amplifier 29 and amplifier 30. Positive signals, should they occur, last only momentarily until system balance is once again resumed.

Increasing negative signals from amplifier 28 and consequently amplifier 30 are indicative of detected porosities falling below the desired set point. This influence ultimately causes the servo-motor 46 to lower the web supporting platform or table 16 and the moving web 10 to intersect the incident laser beams 22 at a larger cross-section of its diverging cone to puncture larger holes in the moving web 10. The reverse action takes place if detected porosity were above the desired set point. Since this system of FIGS. 1 and 2 operates on the back side of the laser beam focal point 23 as shown in FIG. 3, upward table movement decreases web porosity; downward movement increases porosity.

The system of FIGS. 1 and 2 has the ability to automatically position a moving perforated web 10 incident to diverging laser beams 22 to produce changes in porosity of the moving web 10 according to a set point determined by resistor R1 and maintain this porosity regardless of changes in laser beam energy, web characteristics, web speed, or other parameters. This concept of closed-loop control could also be applied to vary laser beam energy to produce the same result.

The operation of the servo-motor 46 is controlled by the action of relay contacts LL, DWN, UL, UP, UPX, DWX, UPY and DWY. An analog signal from amplifier 30 applied to amplifier 40 causes the servo-motor 46 and consequently the web support table 16 to respond linearly such that, in an illustrative embodiment, a zero signal or a momentary positive signal from amplifier 30 moves the support table 16 to its most upward position and a signal of minus ten volts would move the support table 16 to its most downward position. The table 16 moves in direct proportion to the applied signal between zero and minus ten volts.

The table limits are set by the potentiometers R29 and R30. Whenever the table 16 is within its operational limits, the coils LL and UL and thus the associated contacts LL and UL will be energized and closed. This is the result of the servo feedback signal from the resistor R22 which, being linearly proportional to the table position, is compared by operational amplifiers 50 and 52 with the signals from the variable resistors R29 and R30, respectively. Since the positive signal from the resistor R30 is set low for the table upward limit, the greater positive signal from the servo potentiometer R22 will dominate and be inverted by amplifier 52 becoming an amplified negative signal causing transistor T4 to conduct and energize relay coil $L_{UL}$. Amplifier 50 simultaneously compares the feedback signal from the potentiometer R22 with the positive signal from the potentiometer R29 which is set high. The positive signal from the potentiometer R29 dominates the feedback signal from the servopotentiometer R22 and will appear at the output of amplifier 50 as an amplified positive signal causing transistor T3 to conduct and energize relay coil $L_{LL}$.

Relay coils $L_{DWN}$ and $L_{UP}$ respond to the error or difference between the negative signals from amplifier 30 and the positive feedback from servo-potentiometer R22, i.e., amplifier 40 produces positive or negative outputs to energize either the relay coil $L_{DWN}$ or the relay coil $L_{UP}$ via transistors T1 and T2, respectively. Should the signal from the amplifier 30 be more negative than the signal from the potentiometer R22 is positive, a negative error will result and be inverted by amplifier 40 to a positive signal which in turn will activate transistor T1 to energize relay coil $L_{DWN}$. Assuming that the servomotor 46 and its feedback from servopotentiometer R22 fall within the limits set by potentiometers R29 and R30, relay contact DWN will close completing the circuit via relay contact LL, relay coil $L_{DWX}$, and normally closed relay contact UPY. Relay coil $L_{DWX}$ energizes closing contact DWX applying a potential, e.g., plus 24 VDC to the servo-motor 46, causing it to rotate in a direction to move the web support table 16 downward as seen in FIG. 2. This action will continue until the increasing positive voltage from feedback potentiometer R2 and the resulting increase in web porosity reaches a balance at the output of amplifier 40, also indicating a balance between detected porosity and the desired set point signal as derived from the output of amplifier 28. If the lower limit of the support table 16 is reached, the increased positive signal from potentiometer R22 will have reached a higher positive value than that from potentiometer R29 causing amplifier 50 to produce a negative output de-energizing transistor T3 and relay coil $L_{LL}$. Contact LL opens de-energizing relay coil $L_{DWX}$ and opening contact DWX to stop the servo-motor 46. The only further action available would be a signal to ultimately produce upward movement of the table 16. This would result in an inevitable decrease in signal from amplifier 30 which, dominated by the high positive signal from servo-potentiometer R22, causes amplifier 40 to produce an amplified negative signal; transistor T2 now conducts energizing relay coil $L_{UP}$. Since contact UL is closed, the closing of UP contact completes the circuit via relay coil $L_{UPX}$ and normally closed contact DWY. This action causes coil $L_{UPX}$ to energize closing contact UPX. Thus, a voltage of illustratively minus 24 volts is supplied to the servo-motor 46 causing it to rotate in a reverse direction and to provide an upward movement of table 16. Contact UPX remains closed until the resulting error between the set point and the detected porosity signal from amplifier balances with the servo feedback signal from potentiometer R22.

Amplifier 40 actually acts as a reversing switch with a passband or sensitivity determined by the adjustment of potentiometer R19. Amplifiers 50 and 52 act as switching level detectors with a slight hystersis provided by resistors R23 and R28. When system balance is achieved, no output error exists at amplifier 40 and neither relay coil $L_{UP}$ or relay coil $L_{DWN}$ is energized. The servo-motor 46 remains motionless until unbalance reappears.

Figure 5A:
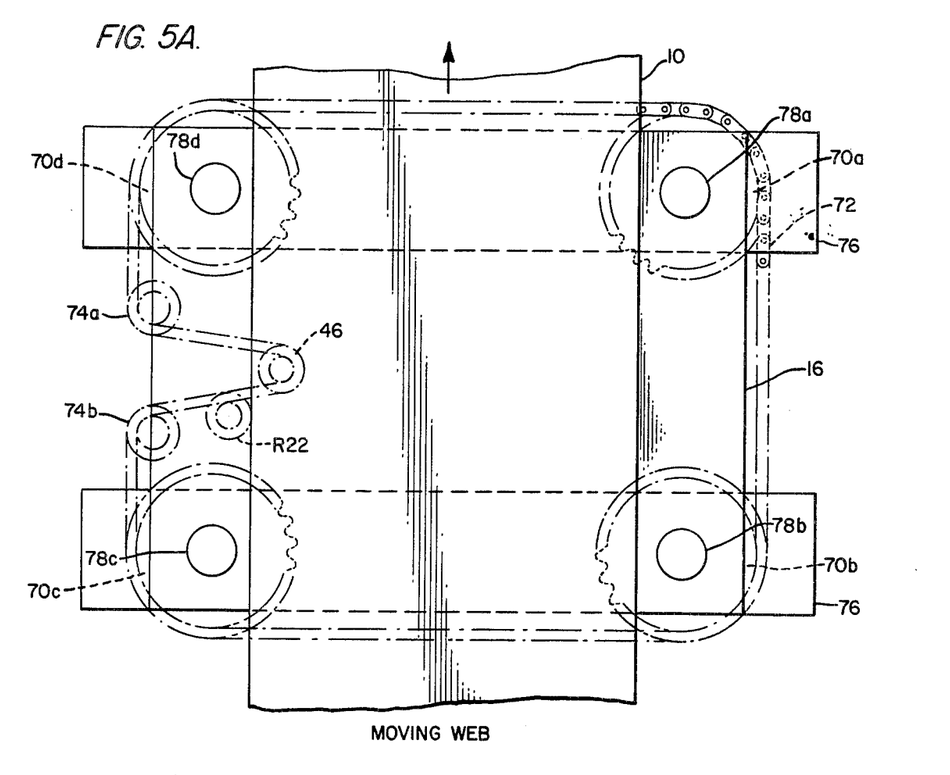
FIGS. 5A and 5B respectively show top and side views of the movable platform and mechanical translator as generally shown in FIG. 1.
Figure 5B:
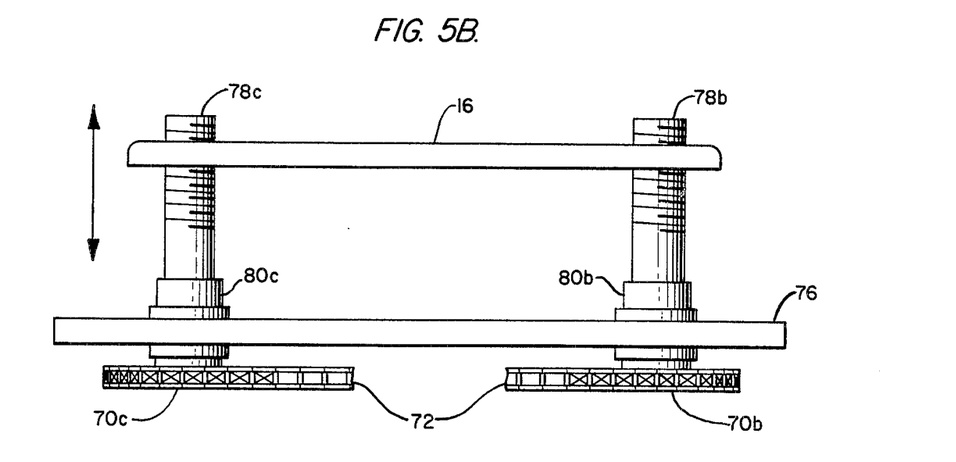

The platform 16 and the mechanical transducer for raising and lowering the platform 16 with respect to the focal points 23 of the beam of radiation, as generally shown in FIG. 1, is shown in detail in FIGS. 5A and 5B. As shown in FIGS. 1 and 5A, the servo-motor 46 is energized to raise or to lower the platform 15 and is coupled by a chain 72 to four sprockets 70a, 70b, 70c and 70d each coupled to its own threaded shaft 78a, 78b, 78c, and 78d, respectively. Each of the shafts 78 are threaded through a corresponding bearing and supporting collar 80a, 80b, 80c and 80d, respectively. As shown in FIG. 5B, the collars 80 are supported upon a support frame 76 as are a pair of idler sprockets 74a and 74b. Thus, as the servo-motor 46 rotates in one direction or the other, the chain is moved to raise or lower the shafts 78 and the platform 16 respectively.

Figure 6A:
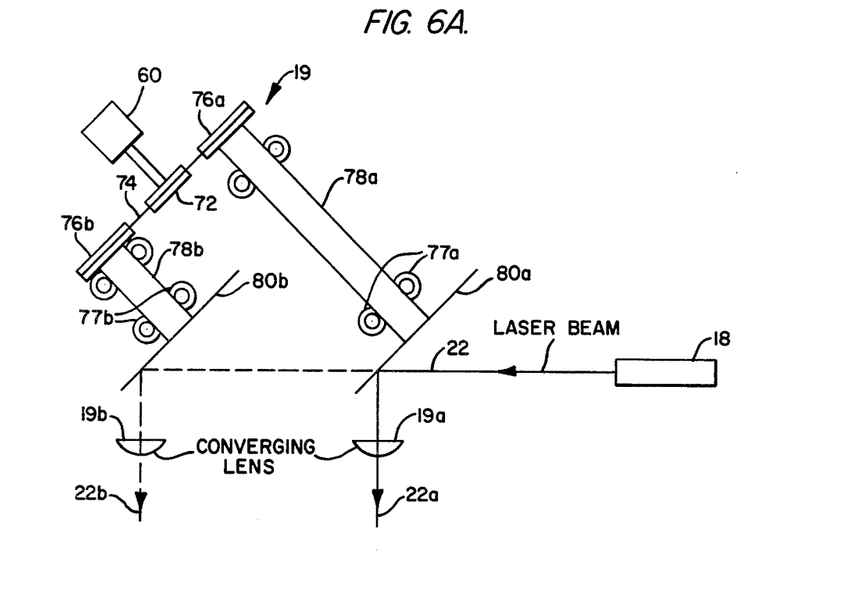
FIGS. 6A and 6B show respectively side and plan views of the laser beam chopper and multiplexer generally shown in FIG. 1.
Figure 6B:
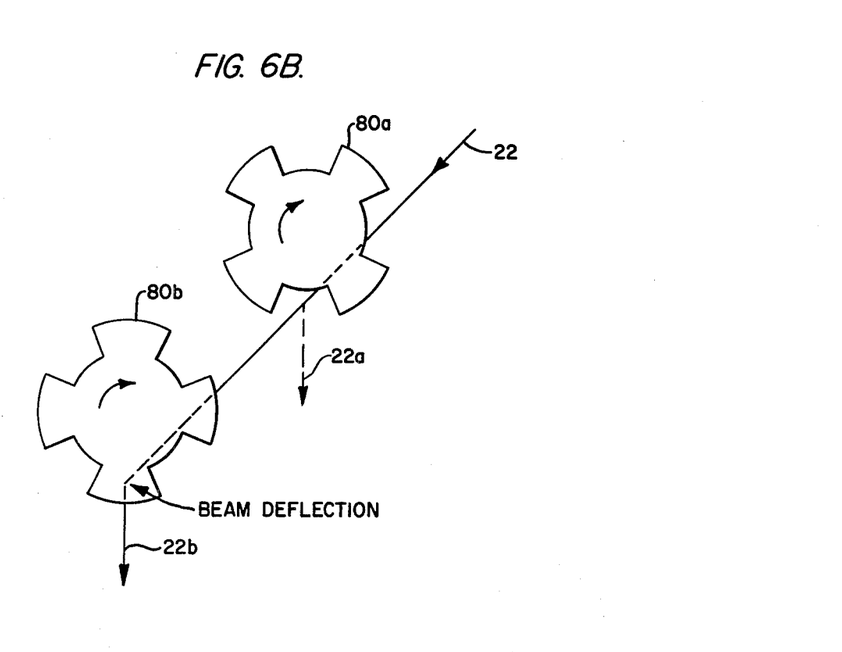

In FIGS. 6A and 6B, the details of the chopper unit 19 are shown. In particular, the source 18 emits a laser beam that is directed on to one of a plurality, e.g., two, of chopper wheels 80a and 80b. As shown more specifically in FIG. 6B, each of the wheels 80 has a plurality of blade sections disposed to intercept the beam 22. As shown in FIGS. 6A and 6B, only one of the blades of the wheels 80a and 80b is disposed at any one time to intercept and to reflect the beam 22 onto the web 10 via lenses 19a and 19b. For example, the wheel 80b has a blade so disposed to intercept the beam 22 and to direct the beam along the direction 22b onto the web 10. As seen in FIG. 6A, each of the beams 22a and 22b are focused by its own converging lens 19a and 19b onto the web 10. The wheels 80a and 80b are driven by the chopper motor 60 which is coupled to a pulley 72, which in turn drives each of the chopper shafts 78a and 78b via belt 74. The belt 74 is disposed about each of a pair of pulleys 76a and 76b for respectively rotating its shaft 78a and 78b. Further, each of the shafts 78a and 78b are journaled to rotate within assemblies of ball bearings 77a and 77b.

Numerous changes may be made in the above described apparatus and the different embodiments of the invention may be made without departing from the spirit thereof; therefore, it is intended that all matter contained in the foregoing description and in the accompanying drawings shall be interpreted as illustrative and not in a limiting sense.

I claim:

1. Apparatus for controlling the porosity of a web of sheet material, comprising:
   (a) a source of a beam of coherent radiation and means for focusing said beam of radiation to a fixed focal point;
   (b) means for directing said web past said beam;
   (c) means for interrupting said beam to produce a plurality of pulses therein, whereby said pulses of coherent radiation produce a corresponding plurality of holes in said web;
   (d) electronic means for setting a reference output indicative of the desired porosity of said web;
   (e) vacuum chamber and transducer means for measuring the resultant web porosity and for providing a corresponding web porosity output;
   (f) an electronic control circuit responsive to the reference output and the web porosity output for providing an error signal indicative of the difference therebetween; and
   (g) a servomechanism responsive to said error signal for controllably moving said web in a direction parallel to said beam, whereby the size of the resultant web hole and therefore porosity are controlled.

2. The apparatus as claimed in claim 1, wherein said servomechanism further comprises a table for receiving and positioning said web with respect to said source, and a servo-motor responsive to said error signal for positioning said table with respect to said source.

3. The apparatus as claimed in claim 2, wherein there is further included a translator mechanism coupled to said table and to said servo-motor for converting the rotational output of said servo-motor for rectilinearly moving said table closer to or farther from said source of coherent radiation.

4. The apparatus as claimed in claim 2, wherein there is included means for sensing the position of said table to provide a signal indicative thereof, and means responsive to said table position signal and to said first-mentioned error signal, to provide a second error signal, said responsive means of paragraph (g) responsive to said second error signal for adjusting the relative position of said web with respect to said fixed focal point.

5. The apparatus as claimed in claim 4, wherein there is further included a servo-amplifier responsive to the second error signal for controlably energizing said servo-motor to rotate in a first direction or in a second direction opposite to said first.

6. The apparatus as claimed in claim 2, wherein there is included means for setting an upper limit and a lower limit to the position of said table, and means responsive to the position of said table when it approaches either said upper or lower limit for deactuating said servo-motor.

7. The apparatus as claimed in claim 1, wherein there is included means for synchronizing the web porosity established by said directing means of said subparagraph (b) and said interrupting means of subparagraph (c) to produce a selected, controlled number of web holes for unit length of travel of said web.

8. The apparatus as claimed in claim 7, wherein said means for synchronizing comprises means for providing a signal indicative of web velocity, and means responsive to an indication of the desired ratio between a set rate of interrupting said beam of coherent radiation and the web velocity, for providing an output signal for controlling said means for interrupting to produce said pulses at a desired rate.

9. The apparatus as claimed in claim 8, wherein said means for interrupting comprises a plurality of rotatable members to produce a plurality of beams of fixed focal length, and motor means coupled to said rotatable members to repeatedly interrupt said beam of coherent radiation.

10. The apparatus as claimed in claim 9, wherein said means for synchronizing comprises adjustable means for providing a synchronization signal indicative of the set ratio of interrupting and web velocity, and said responsive means comprises a multiplier responsive to the synchronization signal and the web velocity signal to provide a signal to said motor means indicative of the desired speed of the rotatable member coupled thereto.

11. Apparatus for controlling the porosity of a web of sheet material, comprising:
   (a) a source of a beam of coherent radiation and means for focusing said beam to a fixed focal point;
   (b) means for directing said web past said beam;
   (c) means for interrupting said beam of radiation, and including a rotatable member and first motor means coupled to rotate said rotatable member to repeatedly interrupt said beam to produce a plurality of pulses therein, whereby said pulses of coherent radiation are directed onto and produce a corresponding plurality of holes in said web as said web is moved therepast by said directing means;
   (d) electronic means for setting a reference output indicative of the desired porosity of said web;
   (e) vacuum chamber and transducer means for measuring the web porosity and for providing a corresponding web porosity output;
   (f) an electronic control circuit responsive to the reference output and the web porosity output for providing an error signal indicative of the difference therebetween;
   (g) a table for receiving and positioning said web as it is directed past said pulses of coherent radiation, and second motor means responsive to said error signal for positioning said table in a direction parallel to said beam, whereby the size of the resultant web hole and therefore its porosity are controlled; and
   (h) means coupled to said web to provide a signal indicative of web velocity to be applied to said first motor means to thereby control the speed of rotation of said rotatable member, to thereby control the desired number of pulses in relationship to the velocity of said web.

12. The apparatus as claimed in claim 11, wherein said means for interrupting includes a second rotatable member coupled to said first motor means, said first mentioned and said second rotatable member being so rotated to produce first and second beams of radiation of fixed focal points to be directed onto said web.

13. Apparatus as claimed in claim 12, wherein there is included at least first and second lenses disposed in a fixed relationship to said source of coherent radiation for focusing said first and second beams of radiation onto said web as it is moved across said table.

* * * * *